United States Patent [19]

Leader et al.

[11] Patent Number: 5,093,266
[45] Date of Patent: Mar. 3, 1992

[54] SENSOR SYSTEM

[75] Inventors: Matthew J. Leader, Long Beach; Tadao Kamiya, Anaheim, both of Calif.

[73] Assignee: Shiley Inc., Irvince, Calif.

[21] Appl. No.: 316,279

[22] Filed: Feb. 27, 1989

Related U.S. Application Data

[62] Division of Ser. No. 12,105, Feb. 6, 1987, Pat. No. 4,833,091.

[51] Int. Cl.$^5$ .............................................. G01N 33/50
[52] U.S. Cl. ...................................... 436/68; 128/634; 128/632; 128/635; 204/416; 204/433; 250/459.1; 250/461.1; 356/39; 422/82.03; 422/82.04; 422/82.06; 422/82.08; 436/133; 436/163; 436/172
[58] Field of Search ............... 422/52, 82.03, 82.08, 422/82.04, 82.06; 436/68, 163, 172, 133; 204/416, 433; 128/632, 635, 634; 250/461.1, 459.1, 373.1, 458.1; 356/39, 40, 407, 441

[56] References Cited

U.S. PATENT DOCUMENTS

| Re. 31,879 | 5/1985 | Lubbers et al. |
| 4,003,707 | 1/1977 | Lubbers et al. |
| 4,041,932 | 8/1977 | Fostick |
| 4,200,110 | 4/1980 | Peterson et al. |
| 4,476,870 | 10/1984 | Peterson et al. |
| 4,495,293 | 1/1985 | Shaffar ................. 436/172 |
| 4,548,907 | 10/1985 | Seitz et al. |
| 4,851,195 | 7/1989 | Matthews et al. ........... 422/82.08 |

OTHER PUBLICATIONS

G. G. Guilbault, "Practical Fluorescence" (1973), pp. 599-600.
Zhang Zhujun et al., Analytica Chimica Acta 160 (1984), pp. 47-55 and 305-309.

Primary Examiner—Robert J. Warden
Assistant Examiner—Timothy M. McMahon
Attorney, Agent, or Firm—Peter C. Richardson; Lawrence C. Akers; Mark Dryer

[57] ABSTRACT

A sensor system for determining the pH or carbon dioxide concentration of a liquid medium comprising, in combination, a pH-insensitive fluorescent indicator and a PH-sensitive fluorescent indicator which act in concert or a single fluorescence indicator which emits fluorescent signals of different wavelengths in different carriers, which system(s) produce diverging signals, the ratio of which provides an accurate and stable determination of the parameter being measured. A method for determining pH and $CO_2$ concentration is also disclosed.

15 Claims, 9 Drawing Sheets

SENSOR SYSTEM

This is a division of application Ser. No. 012,105, filed on Feb. 6, 1987, now U.S. Pat. No. 4,833,091.

BACKGROUND OF THE INVENTION

This invention relates to a sensor system, particularly to a system for determining the pH of a liquid medium and a system for determining the concentration of carbon dioxide in a liquid medium. The invention is also concerned with a method for measuring the concentration of carbon dioxide in a medium.

The measurement of desired parameters in various media, particularly in biological systems, is frequently required. For example, the measurement in blood of pH levels and concentration of gases, particularly oxygen and carbon dioxide, is important during surgical procedures, post-operatively, and during hospitalization under intensive care and many devices for the measurement of said physiological parameters have been suggested in the art.

U.S. Pat. No. 4,003,707, Lubbers et al, and its reissue patent Re 31879 a method and an arrangement for measuring the concentration of gases and the pH value of a sample, e.g. blood, involving the use of a fluorescent indicator at the end of a light-conducting cable which is sealingly covered by or embedded in a selectively permeable diffusion membrane. The radiation transmitted to and emitted from the indicator must be passed through various filtering elements and light elements, including reflectors, beam splitters and amplifiers before any meaningful measurements can be made.

U.S Pat. No. 4,041,932, Fostick, discloses a method whereby blood constituents are monitored by measuring the concentration of gases or fluids collected in an enclosed chamber sealingly attached to a skin "window" formed by the stratum corneum over a small area of the patient's skin. The measurements in the enclosed chamber are made, inter alia, by determining the difference in intensity of light emitted from a fluorescent indicator.

U.S. Pat. Nos. 4,200,110 and 4,476,870, Peterson et al, disclose the use of a pH sensitive indicator in conjunction with a fiber optic pH probe. In each of these patents the dye indicator is enclosed within a selectively permeable membrane envelope.

U.S. Pat. No 4,548,907, Seitz et al, discloses a fluorescent-based optical sensor comprising a membrane immobilized fluorophor secured to one end of a bifurcated fiber optic channel for exposure to the sample to be analyzed.

Many fluorescent indicators sensitive to pH, and thereby useful for $pCO_2$ measurements, are known in the art. Examples of useful fluorescent indicators are disclosed in the above patents and also in "Practical Fluorescence" by George E. Guilbault, (1973) pages 599-600.

Sensor devices using fluorescent indicators may be used for in vitro or in vivo determinations of components in physiological media. For in vitro determinations the size of the device is normally of no consequence, but for in vivo use, the size of the sensor may be extremely critical and there is an increasing need in the art to miniaturize sensor devices, particularly catheter-type devices, for the in vivo determination of components in physiological media, e.g. blood. However, diminution in size of the components of such devices, particularly in the size of the sensor itself, decreases the strength of the signal emitted by the indicator and consequently presents problems in the detection and measurement of said signal. These problems are aggravated when the detector system requires a multiplicity of components, such as filters, beamsplitters and reflectors to isolate and measure the emitted energy. Each of said components reduces the emitted signal strength resulting in a sequential loss of measurable signal. Consequently, the more components present in the system, the weaker the final signal strength.

The problems associated with miniaturization of sensor devices are substantially solved by a device involving a radiation-transmissible junction of optical fibers encased in an opaque radiation reflective jacket as described and claimed in commonly assigned patent application Serial No. 874,927 (U.S. Pat. No. 4,927,222).

With the aid of said device the emission signal from radiation-sensitive indicators, particularly fluorescent indicators of the type disclosed in the prior art references discussed above, may be received substantially unattenuated in a suitable detector without the necessity of filters, beam splitters, reflectors or other light elements used in the prior art.

Another approach for obtaining a meaningful measurement is to use the ratio of two signals which provides a signal with greater resolution than that obtainable from prior art systems based upon a single signal. Zhang ZHUJUN et al in Analytica Chimica Acta 160 (1984) 47-55 and 305-309 disclose that the fluorescent compound 8-hydroxy-1,3,6-pyrenetrisulfonic acid, referred to herein as HPTA, fluoresces when excited by excitation radiation having wavelengths of 470 and 405 nm and the fluorescence emission is sensitive to changes in pH in the physiological range of 6 to 9.

In contrast to the system disclosed by Zhujun et al, which uses two excitation radiations to produce fluorescence, surprisingly, it has now been found that highly accurate, stable determination of pH can be obtained from a single external source of excitation radiation which is used to excite a first fluorescent indicator which in turn emits fluorescent radiation to excite fluorescence emission in a second fluorescent indicator, e.g. HPTA; said first indicator being insensitive to pH.

According to the present invention, a new improved system is obtained by the use of two fluorescent indicators acting in concert or by the use of a single fluorescence indicator which emits fluorescent signals of different wavelengths in different carriers which signals have intensities proportional to the parameter under investigation. Under this approach the parameter being measured is determined by the ratio of two diverging signals which provides greater resolution and a highly accurate, stable determination.

The term "stable" as used herein is intended to mean the stability of the determination with respect to all factors which might influence the measurement other than the parameter being measured. Thus the determination is not affected by, for example, changes in the strength of the excitation radiation, fluctuations in light or temperature or minor equipment defects. Since the quantity being measured is a ratio between two given intensities and this ratio remains constant when the value being measured is constant, irrespective of the actual size of the individual intensities, the resultant determination is necessarily stable.

When the excitation radiation used to actuate the system according this invention is introduced through a device as claimed in U.S. Pat. application Ser. No. 874,927 even greater signal strength and resolution may be obtained.

SUMMARY OF THE INVENTION

In accordance with the present invention there is provided a sensor system for determining the pH of a liquid medium which comprises, in combination, a first fluorescent indicator whose fluorescence emission is insensitive to pH and a second fluorescent indicator whose fluorescence emission is highly sensitive to solution pH, which indicator combination is adapted to respond when a source of excitation radiation of wavelength $\lambda_o$ is applied to the system such that said first fluorescent indicator is selectively excited by said excitation radiation to emit pH-insensitive fluorescence emission at wavelength $\lambda_1$, which emission overlaps the excitation radiation spectrum of said second fluorescent indicator, and said second indicator being excited by said emission radiation of wavelength $\lambda_1$ and in turn emitting a pH-dependent fluorescence emission of wavelength $\lambda_2$, the ratio of intensities of the radiation of wavelengths $\lambda_2/\lambda_2$ providing a highly accurate, stable determination of the pH of said liquid medium.

The invention also provides a method for determining the pH of a liquid medium which comprises contacting said medium with a sensor system comprising, in combination, a first fluorescent indicator whose fluorescence emission is insensitive to pH and a second fluorescent indicator whose fluorescence emmission is highly sensitive to solution pH, subjecting said sensor system to excitation radiation of a predetermined wavelength $\lambda_o$, thereby selectively exciting said first fluorescent indicator to emit a pH-insensitive fluorescence emission at a wavelength of $\lambda_1$, which emission overlaps the excitation radiation spectrum of said second fluorescent indicator and thus excites said second indicator to emit a pH-dependent fluorescence emission of wavelength $\lambda_2$, and measuring the ratio of intensities of the emitted radiation of wavelengths $\lambda_1/\lambda_2$ thereby obtaining a highly accurate, stable determination of the pH of said liquid medium.

The sensor system and method described above are referred to herein as the first embodiment of the invention.

By using the system and method of the invention, enhancement of signal resolution is obtained due to the divergence of the fluorescence emission intensities as a function of pH of the surrounding medium. This phenomenon provides a higher degree of measurement resolution thus providing an increase in measurement accuracy in determining solution pH.

The invention further provides a sensor system for the determination of the concentration of carbon dioxide in a liquid medium which comprises, in combination, a first fluorescent indicator whose fluorescence emission is insensitive to pH and a second fluorescent indicator whose fluorescence emission is highly sensitive to solution pH, which indicator combination is associated with a bicarbonate solution bounded by a carbon dioxide-permeable membrane, and is adapted to respond when a source of excitation radiation of wavelength $\lambda_o$ is applied to the system such that said first fluorescent indicator is selectively excited by said excitation radiation to emit a pH-insensitive fluorescence emission at wavelength $\lambda_1$, which emission overlaps the excitation radiation spectrum of said second fluorescent indicator, said second indicator being excited by said emission radiation of wavelength $\lambda_1$, and in turn emitting a pH-dependent fluorescence emission of wavelength $\lambda_2$, the ratio of intensities of the radiation of wavelengths $\lambda_1/\lambda_2$ providing an indication of the solution pH within the membrane and thereby a highly accurate, stable determination of the concentration of carbon dioxide in the liquid medium.

The invention still further provides a method for determining the concentration of carbon dioxide in a liquid medium which comprises contacting said medium with a sensor system comprising, in combination, a first fluorescent indicator whose fluorescence emission is insensitive to pH and a second fluorescent indicator whose fluorescence emission is highly sensitive to solution pH, which indicators are associated with a bicarbonate solution bounded by a carbon dioxide-permeable membrane, subjecting said sensor system to excitation radiation of predetermined wavelength $\lambda_o$, thereby selectively exciting said first fluorescent indicator to emit a pH-insensitive fluorescence emission at a wavelength of $\lambda_1$, which emission overlaps the excitation radiation spectrum of said second fluorescent indicator and thus excites said second indicator to emit a pH-dependent fluorescence emission of wavelength $\lambda_2$, and measuring the ratio of intensities of the emitted radiation of wavelengths $\lambda_1/\lambda_2$, thereby obtaining an indication of the solution pH within the membrane and thus a highly accurate, stable determination of the concentration of carbon dioxide in the liquid medium.

The sensor system and method for pCO$_2$ determination described above are referred to herein as the second embodiment of the invention.

This second embodiment, as with the first embodiment, provides enhancement of signal resolution due to divergence of fluorescence emission intensities.

The invention yet further provides a method of measuring the concentration of carbon dixoide in a medium by determining the water content in a pH-independent sensor system comprising an optical fiber having a proximal end and an distal end, said distal end having attached thereto a fluorescence indicator embedded in a carrier matrix with a controlled water content, said carrier matrix containing a miscible mixture of water and non-aqueous solvent in controlled proportions and being separated from said medium by a gas-permeable, water-impermeable diffusion membrane, said indicator, when excited by excitation radiation of predetermined wavelength $\lambda_o$, emitting fluorescent emission at a wavelength $\lambda_w$ in the presence of water and at a wavelength $\lambda_s$ the presence of said non-aqueous solvent, the intensity of each emission being dependent upon the ratio of water to non-aqueous solvent present in the system such that the ratio of the intensities of emitted radiation of wavelengths $\lambda_w$ and $\lambda_s$ is therefore proportional to the amount of water present and diffusion of carbon dioxide through said gas-permeable membrane and subsequent reaction with water to deplete the water content of the system induces a change in the intensities of said emissions, which method comprises transmitting through said optical fiber, from a source adjacent to its proximal end, excitation radiation of said predetermined wavelength $\lambda_o$, measuring the ratio of the intensities of the emitted radiation of wavelengths $\lambda_w$ and $\lambda s$, thereby obtaining a determination of the water content and thus a measurement of the carbon dioxide concentration in the surrounding medium.

The above-described method of measuring pCO$_2$ as a function of the water content in a pH-independent sensor system and the system used in such method is referred to herein as the third embodiment of the invention.

Here again, enhancement of signal resolution is obtained from divergence of fluorescence emission intensities.

DETAILED DESCRIPTION OF THE INVENTION

The sensor system of the first embodiment of the invention preferably includes an optical fiber having a distal end and a proximal end, in which said combination of fluorescent indicators is attached to said distal end and said proximal end is adapted to receive excitation radiation from s-aid source of excitation radiation.

The first fluorescent indicator, which is insensitive to pH, is preferably 6,7-dimethoxycoumarin or a pH-insensitive coumarin derivative. A typical coumarin derivative is beta-methylumbelliferone, particularly in the form where it chemically bonded to an acrylic polymer. The pH sensitivity of the umbellilferone polymer may be retarded by reacting the polymer solution with an excess of cross-linking agent such as poly (acrylic acid).

The particularly preferred indicator for the purpose of the present invention is 6,7-dimethoxycoumarin which, when excited by excitation radiation having a wavelength of 337 nm emits fluorescent radiation at a wavelength of 435 nm. The characteristic excitation and emission spectra of 6,7-dimethoxycoumarin are illustrated in the accompanying drawings as described hereinafter.

It is to be understood that when reference is made herein to a particular wavelength, for example with respect to excitation or emission, it is intended to mean that wavelength which is most representative of the condition being described; most typically the peak of a curve illustrating the spectrum which fully represents said condition. Thus, as shown by the curve for the excitation spectrum, 6,7-dimethoxycoumarin is excited by radiation over a spectrum of wavelengths from 310 to 380 with an optimum excitation at the peak wavelength of 337 nm. For convenience, unless otherwise defined, the wavelengths quoted herein are the peak wavelengths for the phenomenon in question.

The preferred second indicator used in the first embodiment of the invention is HPTA.

In the preferred first embodiment of the invention excitation radiation having a wavelength, i.e. a peak wavelength, $\lambda_o$, of 337 nm, for example from a nitrogen gas laser, is transmitted from the proximal end of an optical fiber through the distal end where it excites a first indicator, preferably 6,7-dimethoxycoumarin, which emits fluorescent radiation having a wavelength, $\lambda_1$, of 435 nm. This fluorescence emission, in turn, excites the second indicator, preferably HPTA, to emit fluorescent radiation having a wavelength, $\lambda_2$, of 510 nm.

The intensity of the fluorescence emission of wavelength $\lambda_2$ (510 nm) is dependent upon the intensity of the excitation emission of wavelength and upon the pH of the surrounding liquid medium, so that measurement of the ratio of the intensities of the emitted radiation of wavelengths $\lambda_1/\lambda_2$ gives a highly accurate, stable determination of the pH of said liquid medium.

It is to be noted that although the intensity of the fluorescence emission of wavelength $\lambda_1$, derived from the pH-insensitive first-indicator, is itself independent of the pH of the medium, the fact that this intensity is affected by energy absorbed by the second indicator, which is pH-sensitive, means that the ratio derived from the peak of the emission spectrum curve of the first indicator and the isobestic point between the two emission curves (as described in detail hereinafter with reference to the drawings) also may be used to give an accurate, stable determination of the pH of the liquid medium.

The sensor system of the second embodiment of the invention preferably includes an optical fiber having a distal end and a proximal end, in which said combination of fluorescent indicators, bicarbonate solution and membrane is attached to said distal end and said proximal end is adapted to receive excitation radiation from said source of excitation radiation.

As in the first embodiment, the preferred first fluorescent indicator is 6,7-dimethoxycoumarin or a pH-insensitive coumarin derivative, with 6,7-dimethoxycoumarin being particularly preferred.

Also the particularly preferred second fluorescent indicator is HPTA.

In a particularly preferred form of the second embodiment the 6,7-dimethoxycoumarin is directly bonded to the distal end of an optical fiber and HPTA is suspended in a gel of carboxymethyl cellulose containing a bicarbonate solution, preferably aqueous sodium bicarbonate solution, which gel is bounded by a silicone rubber membrane.

The method of the second embodiment is preferably carried out by transmitting excitation radiation having a wavelength $\lambda_o$, of 337 nm from a nitrogen gas laser through the optical fiber from its proximal end to its distal end where it excites the 6,7-dimethoxycoumarin to emit fluorescent radiation having a wavelength $\lambda_1$, of 435 nm. This fluorescence emission, in turn, excites the HPTA to emit fluorescent radiation at a wavelength, $\lambda_2$, of 510 nm.

When the sensor is immersed in a liquid medium containing carbon dioxide, the latter permeates through the silicone rubber membrane and reacts with the bicarbonate solution thereby altering the pH of the solution around the sensor. The intensity of the fluorescence emission of wavelength $\lambda_2$ (512 nm) is dependent upon the intensity of the excitation emission of wavelength $\lambda_1$ and upon the pH of said surrounding solution. Therefore, measurement of the ratio of the intensities of the emitted radiation of wavelengths $\lambda_1/\lambda_2$ provides an indication of the solution pH within the membrane and thus a highly accurate, stable determination of the concentration of carbon dioxide ($pCO_2$) in the liquid medium.

DESCRIPTION OF THE DRAWINGS

The accompanying drawings comprise graphs illustrating excitation and emission spectra of the indicators used in the sensors of the invention.

Figure 1:
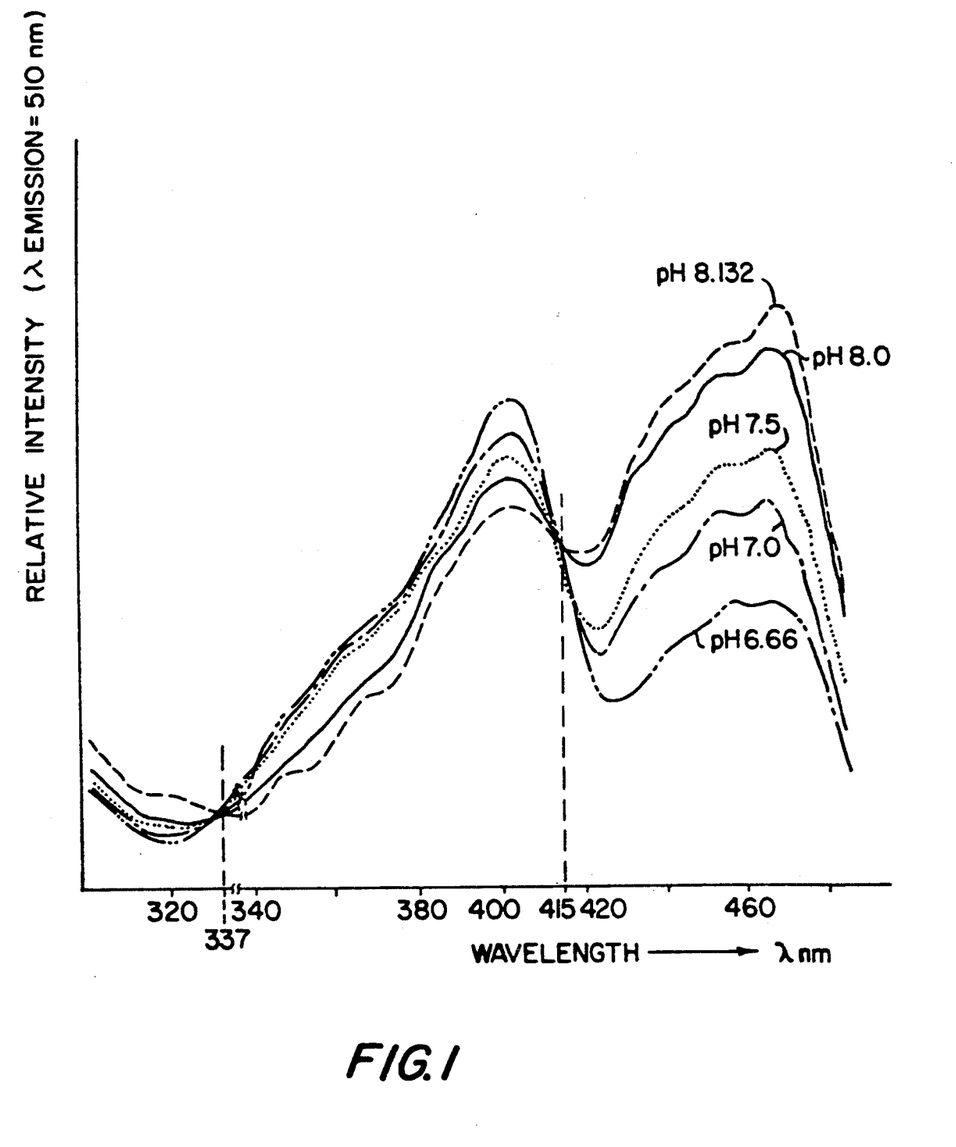
FIG. 1 illustrates excitation spectra for HPTA at varying pH levels.

The excitation spectra for HPTA illustrated in FIG. 1 of the drawings taken over a wavelength range of 300 to 485 nm show that the intensity of the excitation radiation, which is a function of the area under the curve and is proportional to the height of the curve in each case, varies according to the pH of the surrounding medium. In this case the pH was varied from 6.66 to 8.132. Isobestic points were observed at 337 nm and 415 nm. The peak wavelength of the emission from HPTA subjected to the said excitation radiation was 510 nm (not shown).

Figure 2:
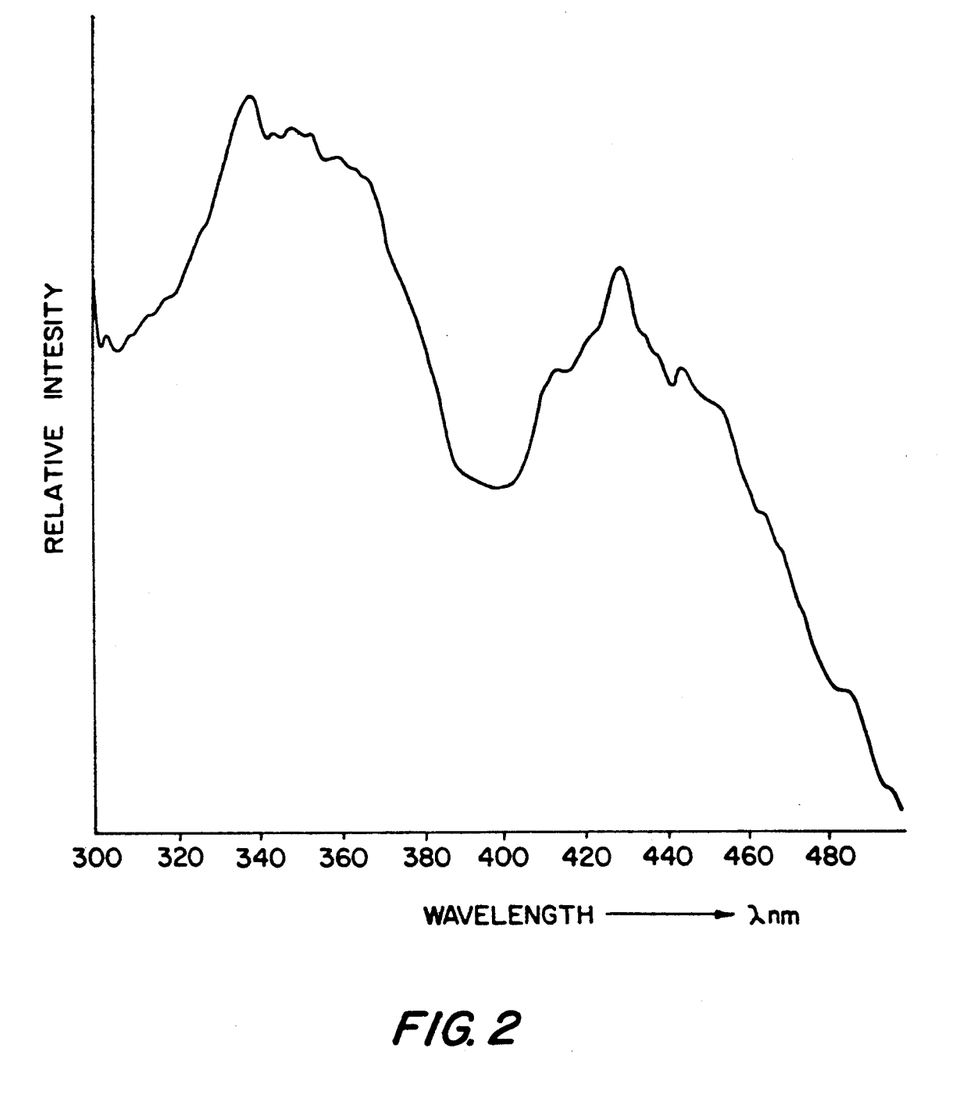
FIGS. 2 illustrates pH-insensitive excitation and emission spectra of dimethoxycoumarin in a solution of bicarbonate and ethylene glycol.

FIG. 2 of the drawings illustrates excitations and emission spectra for dimethoxy coumarin in a solution of sodium bicarbonate and ethylene glycol. The concentration of dimethoxy coumarin is about $10^{-2}$M. The excitation spectrum exhibits a peak at a wavelength of about 340 nm and the emission spectrum has a peak at a wavelength of about 427 nm. The emission fluorescence is pH insensitive. It will be noted that the wavelength of the fluorescence emission for dimethoxycoumarin overlaps the wavelength of the excitation radiation for HPTA as illustrated in FIG. 1.

Figure 3:
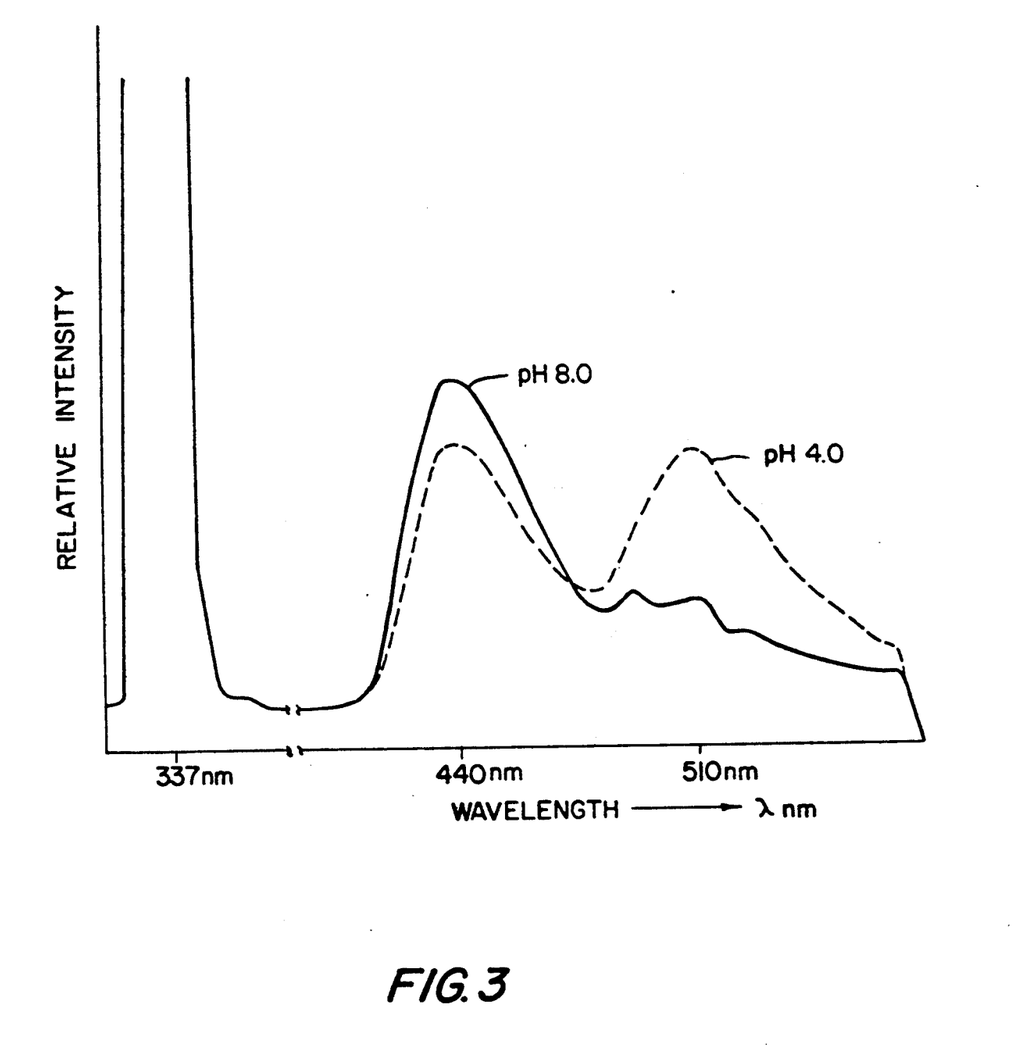
FIG. 3 illustrates spectra for HPTA in ethylene glycol at different pH levels.

FIG. 3 illustrates spectra for HPTA in ethylene glycol at pH 8.0 and pH 4.0, respectively. The HPTA is dissolved in ethylene glycol, one drop of pH 8.0 buffer is added and the solution is irradiated from a nitrogen laser with radiation of wavelength 337 nm. Two fluorescent emissions at wavelengths 440 nm and 510 nm are observed. One drop of pH 4.0 buffer is then added and the intensity of the spectra changes as illustrated in FIG. 3. A peak at 510 nm appeared with the addition of water to the system, regardless of the pH.

Figure 4:
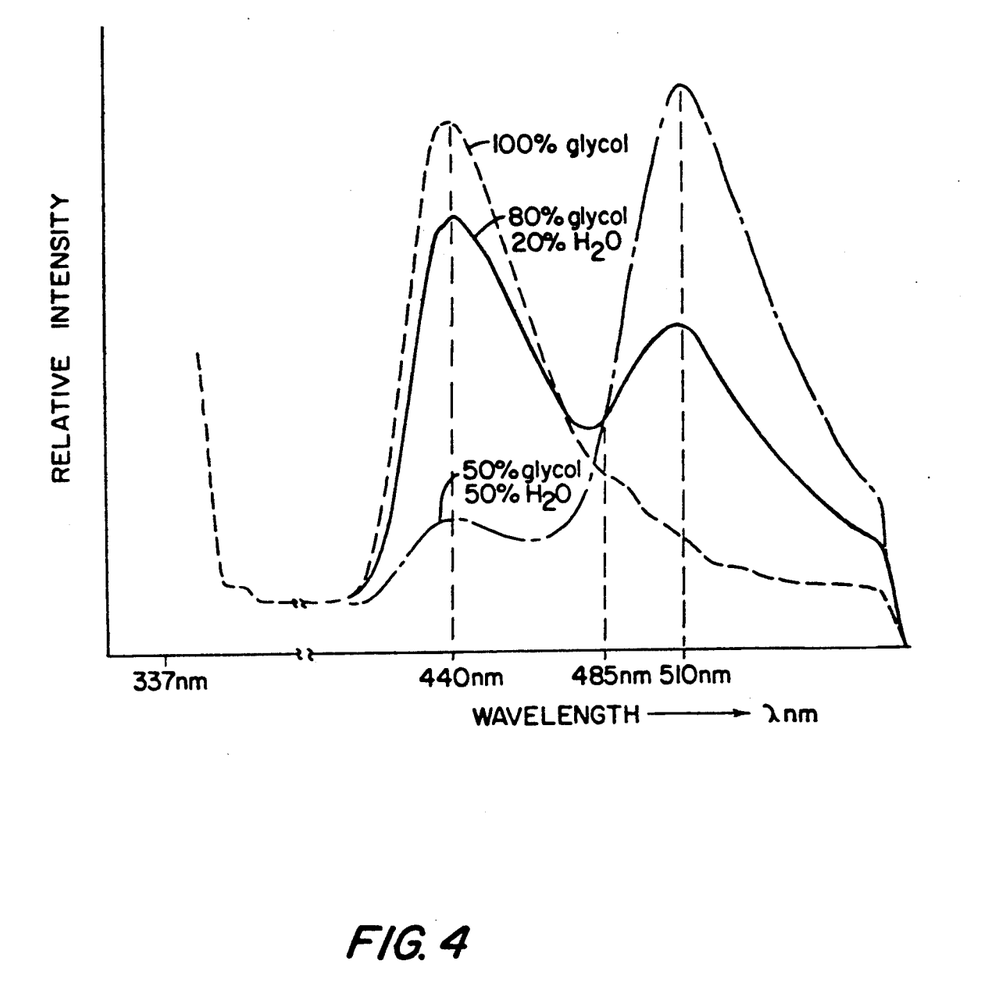
FIG. 4 illustrates spectra for HPTA in different solvent mixtures.

FIG. 4 illustrates spectra of HPTA in different mixtures of ethylene glycol and water. $10^{-M}$ HPTA was dissolved in solution mixtures comprising, respectively, 100% ethylene glycol, 80% glycol/20% water and 50% glycol/50% water. Drops of each solution in turn were put on the tips of optical fibers and the HPTA was excited to fluoresce at a wavelength of 510 nm. The results are shown graphically in FIG. 4.

Additional results were obtained in a similar manner for solutions comprising 20% glycol/80% water and 100% water. The results for all runs are given in the following Table I.

TABLE I

| Solvent | Relative Intensity I (Blue) $\lambda = 440$ nm | Relative Intensity I (Green) $\lambda = 510$ nm | Ratio | 1/Ratio |
|---|---|---|---|---|
| 100% ethylene glycol | 85.63 | 11.66 | 7.34 | 0.1362 |
| 80/20 glycol/water | 69.97 | 49.64 | 1.41 | 0.7092 |
| 50/50 glycol/water | 16.33 | 92.30 | 0.177 | 5.65 |
| 20/80 glycol/water | 5.33 | 83.30 | 0.064 | 15.63 |
| 100% water | 5.33 | 111.96 | 0.048 | 20.83 |

Figure 5:
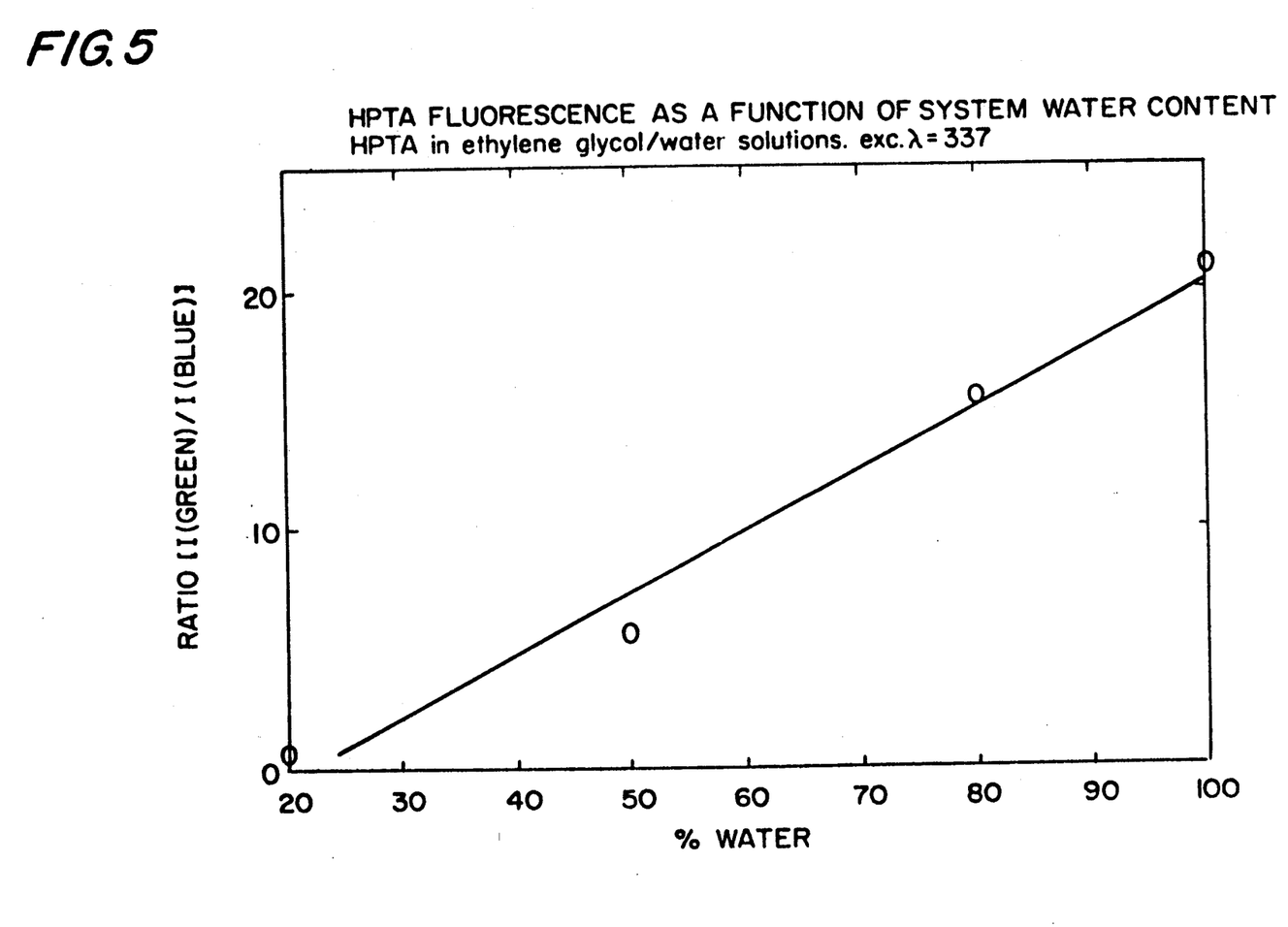
FIG. 5 is a graph showing HPTA fluorescence as a function of the water content of the system.

The fluorescence of HPTA as a function of the water content of the solvent system is illustrated graphically in FIG. 5. Using excitation radiation of wavelength −337 nm the ratio of the fluorescence peaks I(GREEN)/I(BLUE) at $\lambda=510$ nm and $\lambda=440$ nm, respectively, was graphed for HPTA in ethylene glycol/water solutions of varying concentrations. The resulting graph indicates that the ratio of intensities increases substantially linearly as the water content of the solution increases.

Figure 6:
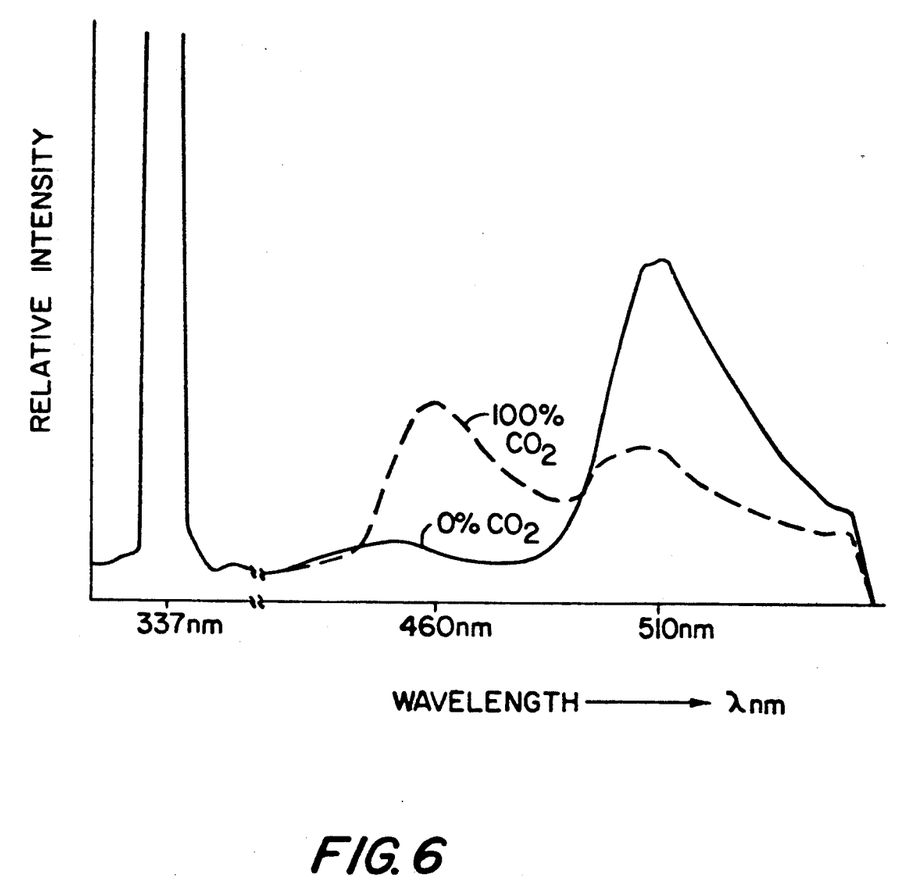
FIG. 6 and FIG. 7 illustrate spectra indicating $pCO_2$ by a sensor system according to the invention.
Figure 7:
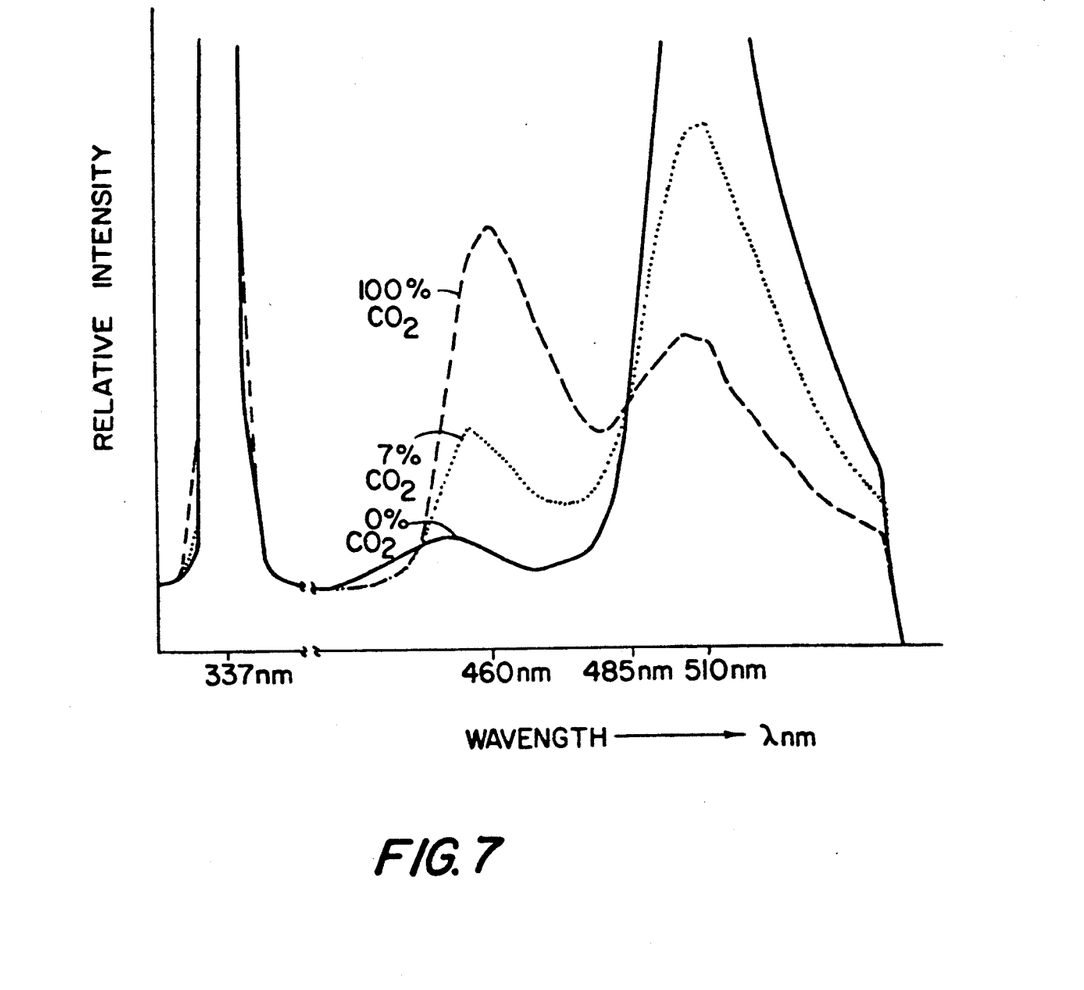

FIGS. 6 and 7 illustrate results obtained by performing the invention as illustrated in the following Examples.

EXAMPLE 1

A mixture of 1:1 dimethoxycoumarin:HPTA both at a concentration of $10^{-3}$M was dissolved in carboxymethyl-cellulose (CMC) and 5mM of sodium bicarbonate with the addition of 0.25 ml ethylene glycol to dissolve the dimethoxycoumarin.

A carbon dioxide sensor was formed by depositing the resulting gel on the tip of an optical fiber formed by fused silica having a diameter of 400 $\mu$m, and enveloping the gel in a carbon dioxide permeable silicone rubber membrane.

The sensor was irradiated with excitation radiation of wavelength 337 nm from nitrogen laser firing at 2 pulse/second. The fluroescence emission was detected with a linear array photodiode and with an oscilloscope set to 0.1 volt/div at 2 ms/div.

A number of runs were conducted at varying carbon dioxide concentrations and the results for 0% $CO_2$ and 100% $CO_2$ are illustrated graphically in FIG. 6 and are set out numerically in the following Table II.

TABLE II

| % $CO_2$ | I (Blue) | I (Green) | Ratio |
|---|---|---|---|
| 0 | 5.66 | 53.97 | 9.53 |
| 100 | 30.32 | 20.99 | 0.69 |

EXAMPLE 2

A gel containing mixture of 1:1 dimethoxycoumarin:HPTA at a concentration of $10^{-3}$ in CMC and 5mM of sodium bicarbonate was made up in a similar manner to that described in Example 1 and this gel was used to form a carbon dioxide sensor also as described in Example 1.

A number of runs were conducted at varying carbon dioxide concentrations and the results are illustrated graphically in FIG. 7 and set out numerically in the following Table III.

TABLE III

| % $CO_2$ | Baseline (COUM) | Baseline (HPTA) | IM (COUM) | IM (HPTA) | Ratio (HPTA/COUM) |
|---|---|---|---|---|---|
| 0% | 9.5 | 10.5 | 20.99 | 150.93 | 12.22 |
| 7% | 9.5 | 10.5 | 40.65 | 97.29 | 2.79 |
| 100% | 8.5 | 10 | 78.63 | 57.64 | 0.68 |

The results given in the above Examples show the accuracy with which quantitative results can be obtained using the sensor system according to the invention.

EXAMPLE 3

This Example illustrates a carbon dioxide sensor utilizing the relationship between the water content of the system and the carbon dioxide concentration. HPTA was dissolved in a 50/50 mixture of ethylene glycol and water and the solution embedded in a carboxymethylcellulose gel. This gel was deposited on the tip of an optical fiber and enveloped in a carbon dioxide permeable silicone rubber membrane to form a carbon dioxide sensor.

Figure 8:
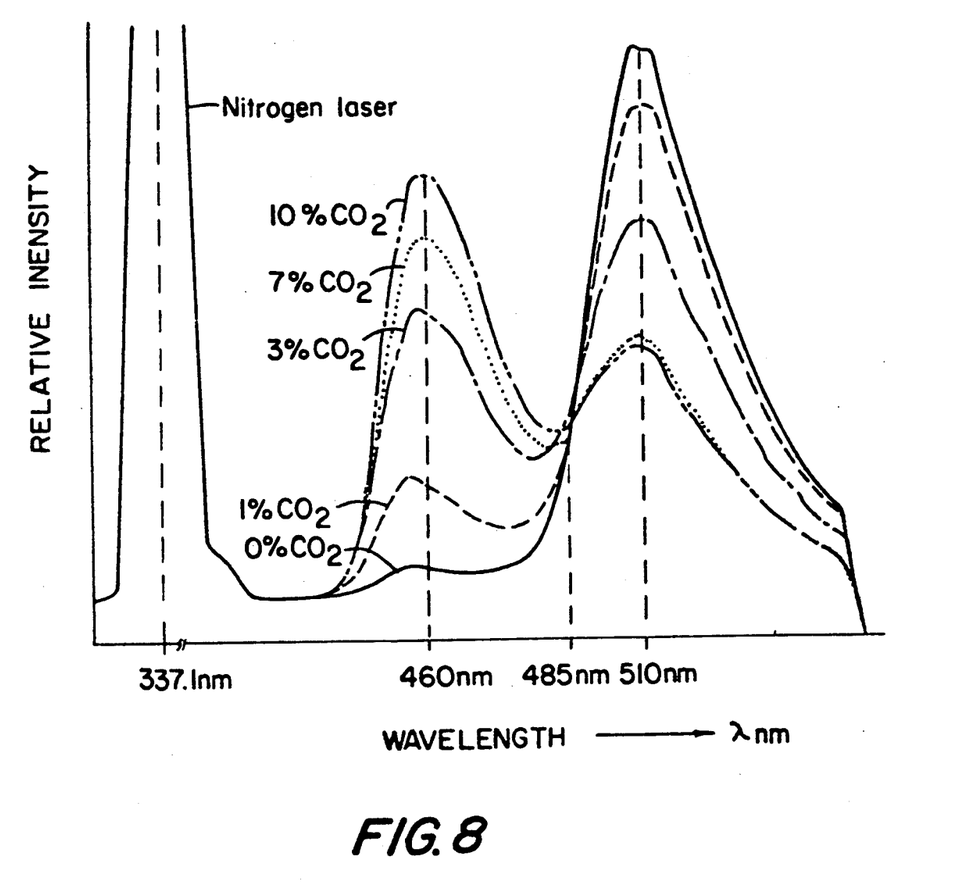
FIG. 8 illustrates spectra for varying carbon dioxide concentrations using HPTA in a 50/50 ethylene glycol/water solution

The sensor was irradiated with radiation of wavelength 337 nm from a nitrogen laser at varying concentrations of carbon dioxide. The results are shown in FIG. 8.

It will be seen that the ratio of intensities of the fluorescence emissions at peak wavelengths of 460 nm and 510 nm is dependent upon the carbon dioxide concentration. The spectra exhibit an isobestic point at 485 nm.

Figure 9:
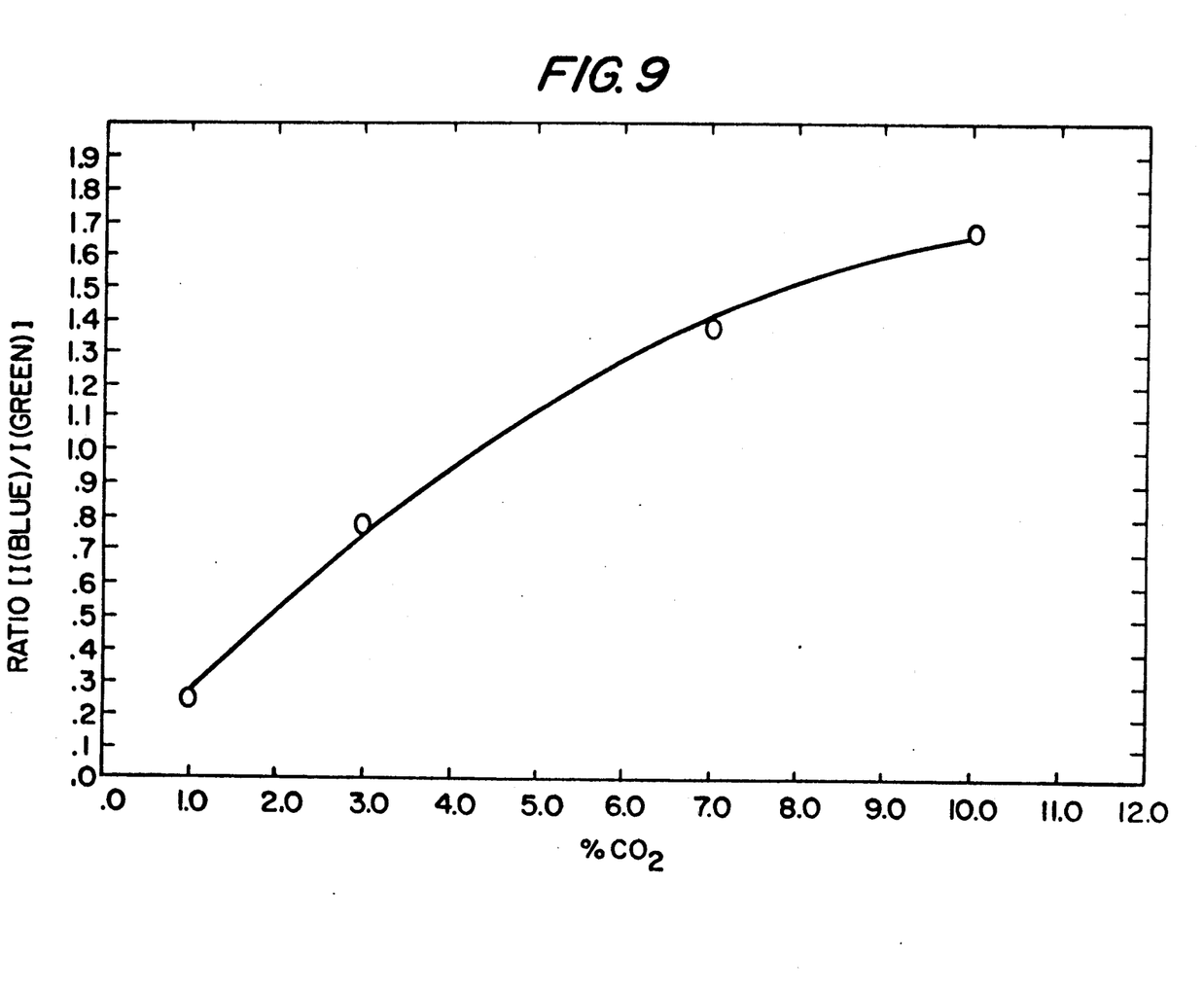
FIG. 9 is a graph showing the relationship between the ratio of fluorescence intensity and carbon dioxide concentration.

The fluorescence ratio as a function of carbon dioxide concentration is illustrated in FIG. 9.

This Example illustrates the way in which a carbon dioxide determination can be obtained as a function of the water content of the sensor.

We claim:

1. A sensor system for determining the pH of a liquid medium which comprises, in combination, a first fluorescent indicator whose fluorescence emission is insensitive to pH and a second fluorescent indicator whose fluorescence emission is highly sensitive to solution pH, which indicator combination is adapted to respond when a source of excitation radiation of wavelength $\lambda_o$ is applied to the system such that said first fluorescent indicator is selectively excited by said excitation radiation to emit pH-insensitive fluorescence emission at wavelength $\lambda_1$, which emission overlaps the excitation radiation spectrum of said second fluorescent indicator, and said second indicator being excited by said emission radiation of wavelength $\lambda_1$ and in turn emitting a pH-dependent fluorescence emission of wavelength $\lambda_2$, the ratio of intensities of the radiation of wavelengths $\lambda_1/\lambda_2$ providing a highly accurate, stable determination of the pH of said liquid medium.

2. A sensor system according to claim 1, which includes an optical fiber having a distal end and a proximal end and in which said combination of fluorescent indicators is attached to said distal end and said proximal end is adapted to receive excitation radiation from said source.

3. A sensor system according to claim 1, in which said first fluorescent indicator is 6,7-dimethoxycoumarin or a pH- insensitive coumarin derivative.

4. A sensor system according to claim 3, in which said second fluorescent indicator is 8-hydroxy-1,3, 6-pyrenetrisulfonic acid (HPTA).

5. A method for determining the pH of a liquid medium which comprises contacting said medium with a sensor system comprising, in combination, a first fluorescent indicator whose fluorescence emission is insensitive to pH and a second fluorescent indicator whose fluorescence emission is highly sensitive to solution pH, subjecting said sensor system to excitation radiation of a predetermined wavelength $\lambda_o$, thereby selectively exciting said first fluorescent indicator to emit a pH-insensitive fluorescence emission at a wavelength of $\lambda_1$, which emission overlaps the excitation radiation spectrum of said second fluorescent indicator and thus excites said second indicator to emit a pH-dependent fluorescence emission of wavelength $\lambda_2$, and measuring either (i) the ratio of intensities of the emitted radiation of wavelengths $\lambda_1/\lambda_2$, or (ii) the ratio derived from the intensity of the emitted radiation of wavelength $\lambda_1$ and the intensity at the isobestic point between the emission curves of said first and second indications, thereby obtaining a highly accurate, stable determination of the pH of said liquid medium.

6. A method according to claim 5, in which the sensor system includes an optical fiber having a distal end and a proximal end, said combination of said first and second fluorescent indicators is attached to the distal end of said optical fiber and said proximal end is adapted to receive excitation radiation from an appropriate source.

7. A method according to claim 6, in which said excitation radiation is laser radiation of wavelength, $\lambda_o$, 337 nm, said first fluorescent indicator is 6, 7-dimethoxycoumarin which emits fluorescent radiation of wavelength, $\lambda_{1,}$ 435 nm and said second, pH-sensitive, fluorescent indicator is 8-hydroxy-1, 3, 6-pyrenetrisulfonic acid which emits fluorescent radiation of wavelength, $\lambda_{2,}$ 510 nm.

8. A sensor system for the determination of the concentration of carbon dioxide in a liquid medium which comprises, in combination, a first fluorescent indicator whose fluorescence emission is insensitive to pH and a second fluorescent indicator whose fluorescent emission is highly sensitive to solution pH, which indicator combination is associated with a bicarbonate solution bounded by a carbon dioxide-permeable membrane, and is adapted to respond when a source of excitation radiation of wavelength $\lambda_o$ is applied to the system such that said first fluorescent indicator is selectively excited by said excitation radiation to emit a pH-insensitive fluorescence emission at wavelength $\lambda_1$, which emission overlaps the excitation radiation spectrum of said second fluorescent indicator, said second indicator being excited by said emission radiation of wavelength $\lambda_1$, and in turn emitting a pH-dependent fluorescence emission of wavelength $\lambda_2$, the ratio of intensities of the radiation of wavelengths $\lambda_1/\lambda_2$ providing an indication of the solution pH within the membrane and thereby a highly accurate, stable determination of the concentration of carbon dioxide in the liquid medium.

9. A sensor system according to claim 8, which includes an optical fiber having a distal end and a proximal end and in which said combination of fluorescent indicators, bicarbonate solution and membrane is attached to said distal end and said proximal end is adapted to receive excitation radiation from said source.

10. A sensor system according to claim 9, in which said first fluorescent indicator is 6, 7-dimethoxycoumarin or a pH-insensitive coumarin derivative.

11. A sensor system according to claim 10, in which said second fluorescent indicator is 8-hydroxy-1, 3, 6-pyrenetrisulfonic acid.

12. A sensor system according to claim 11, in which said first fluorescent indicator is bonded directly to said optical fiber and said second fluorescent indicator is suspended in a gel of carboxymethyl cellulose containing said bicarbonate solution and bounded by a silicone rubber membrane.

13. A method for determining the concentration of carbon dioxide in a liquid medium which comprises contacting said medium with a sensor system comprising, in combination, a first fluorescent indicator whose fluorescence emission is insensitive to pH and a second fluorescent indicator whose fluorescence emission is highly sensitive to solution pH, which indicators are associated with a bicarbonate solution bounded by a carbon dioxide-permeable membrane, subjecting said sensor system to excitation radiation of a predetermined wavelength $\lambda_o$, thereby selectively exciting said first fluorescent indicator to emit a pH-insensitive fluorescence emission at a wavelength of $\lambda_1$, which emission overlaps the excitation radiation spectrum of said second fluorescent indicator and thus excites said second indicator to emit a pH-dependent fluorescent emission of wavelength $\lambda_2$, and measuring either (i) the ratio of intensities of the emitted radiation of wavelengths $\lambda_1/\lambda_2$, or (ii) the ratio derived from the intensity of the emitted radiation of wavelength $\lambda_1$ and the intensity at the isobestic point between the emission curves of said first and second indications, thereby obtaining an indication of the solution pH within the membrane and thus a highly accurate, stable determination of the concentration of carbon dioxide in the liquid medium.

14. A method according to claim 13, in which the sensor system includes an optical fiber having a distal end and a proximal end, said combination of said first and second indicators, bicarbonate solution and membrane is attached to said distal end and said excitation radiation is transmitted, from a source adjacent to said proximal end, through said optical fiber from said proximal end to said distal end.

15. A method according to claim 14, in which said excitation radiation is laser radiation of wavelength, $\lambda_o$, 337 nm, said first fluorescent indicator is 6,7-dimethoxycoumarin which emits fluorescent radiation wavelength, $\lambda_1$, 435 nm and said second, pH-sensitive, fluorescent indicator is 8-hydroxy-1, 3, 6-pyrenetrisulfonic acid which emits fluorescent radiation of wavelength, $\lambda_2$, 510 nm.

* * * * *